United States Patent [19]

Barthelemy

[11] 4,250,307

[45] Feb. 10, 1981

[54] PROCESS FOR THE PREPARATION OF 7-AMINO-CEPHALOSPORANIC ACID

[75] Inventor: Pierre Barthelemy, Barbery, France

[73] Assignee: Roussel Uclaf, Paris, France

[21] Appl. No.: 79,800

[22] Filed: Sep. 28, 1979

Related U.S. Application Data

[62] Division of Ser. No. 940,274, Sep. 7, 1978, Pat. No. 4,189,574.

[30] Foreign Application Priority Data

Sep. 29, 1977 [FR] France ................. 77 29303

[51] Int. Cl.$^3$ ........................................... C07D 501/18
[52] U.S. Cl. ................................... 544/030; 424/246
[58] Field of Search ......................................... 544/30

[56] References Cited

U.S. PATENT DOCUMENTS 3,843,642  10/1974  Jackson et al. ................... 544/30
3,853,863  12/1974  Jackson et al. ................... 544/30

Primary Examiner—Nicholas S. Rizzo

Attorney, Agent, or Firm—Hammond & Littell, Weissenberger and Muserlian

[57] ABSTRACT

A novel compound selected from the group consisting of the compound of the formula

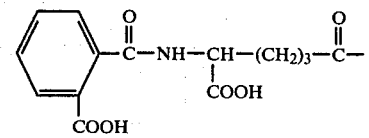

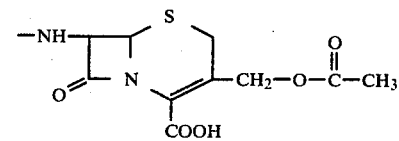

the metal salts, the ammonium salt and the salts with nitrogen bases, a process for the preparation of the said compounds and a process for the preparation of 7-amino-cephalosporanic acid starting from a compound of formula I.

3 Claims, No Drawings

PROCESS FOR THE PREPARATION OF 7-AMINO-CEPHALOSPORANIC ACID

PRIOR APPLICATION

This application is a division of my copending, commonly assigned U.S. patent application Ser. No. 940,274, filed Sept. 7, 1978, now U.S. Pat. No. 4,189,574.

STATE OF THE ART

Cephalosporin C is known to be a very important compound which is used in the preparation of 7-amino-cephalosporanic acid which is used to prepare by hemisynthesis novel cephalosporins. It is also known that due to its amphoteric nature, cephalosporin C is difficult to extract from fermentation medium from which it is produced. Many procedures have been described in the literature to effect this extraction and to obtain as directly as possible 7-amino-cephalosporanic acid.

It has been proposed to isolate cephalosporin C in the form of N-substituted derivatives prepared in situ in the fermentation medium and then to cleave the N-substituted derivative of cephalosporin C to obtain 7-amino-cephalosporanic acid. French Pat. No. 1,394,820 and Helvetica chimica Acta, Vol. 51, Fasci 5 (1968), p. 1108–1119 describe the preparation of a number of derivatives in which the amino function of the aminoadipic chain of cephalosporin C is blocked with lower alkyl, aryl or acyl groups. The latter reference describes on pages 1112–1113 the preparation of phthalimido-cephalosporin C (compound 10) by reacting cephalosporin C with N-carbethoxy-phthalimide in an aqueous solution in the presence of an organic solvent. Other derivatives such as benzamido-cephalosporin C are also described.

The preparation of these cephalosporin C derivatives generally present inconveniences due to expensive starting materials and the necessity of reaction in the presence of organic solvents such as acetone which implies a further treatment of the mother liquor to remove the organic solvent.

OBJECTS OF THE INVENTION

It is an object of the invention to provide the novel derivative of cephalosporin C of formula I and its salts and a novel process for their preparation using inexpensive, readily available starting materials and without the use of organic solvents.

It is another object of the invention to provide a novel process for the preparation of 7-amino cephalosporanic acid.

These and other objects and advantages of the invention will become obvious from the following detailed description.

THE INVENTION

The novel derivatives of cephalosporin C of the invention are selected from the group consisting of the compound of the formula

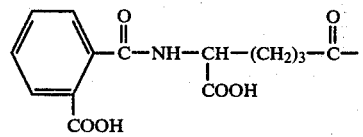

-continued

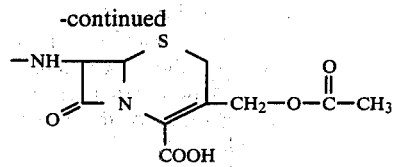

the metal salts, the ammonium salt and the salts with the nitrogen bases.

Examples of suitable metal salts are alkali metals such as sodium, potassium and lithium and alkaline earth metals such as calcium. Examples of suitable bases for the addition salts are ammonium, amines such as monomethylamine, diethylamine, triethylamine, lysine, arginine and triethanolamine and quaternary ammonium salts such as hyamine. Especially preferred is the sodium salt of 3-[(acetyloxy)-methyl]-7-{[5-[[(2-carboxyphenyl)-carbonyl]-amino]-5-carboxy-1-oxopentyl]-amino}-8-oxo-5-thia-1-aza-bicyclo-[4,2,0]-oct-2-ene-2-carboxylic acid.

The novel process of the invention for the preparation of a compound of formula I or its salts comprises reacting cephalosporin C of the formula

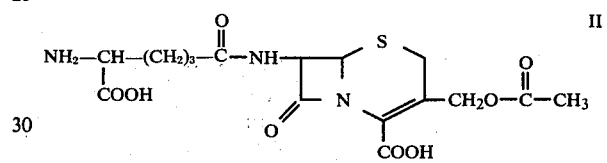

or a salt thereof with phthalic anhydride in an aqueous solution and after having salified the product, if necessary, extracting the product of formula I or a salt from the reaction mixture.

The salts of cephalosporin C used in the process are preferably the alkali metal salts such as potassium or sodium although the ammonium salt may also be used. The aqueous solution of cephalosporin C or its salts is preferably the fermentation medium used to produce cephalosporin C as well as a fermentation medium enriched in cephalosporin C or its salts.

The extraction of the compound of formula I or its salts may be effected with a low molecular weight alkanol such as n-butanol, isobutanol or sec-butanol. The compound of formula I can be directly extracted in the form of a salt after alkalinization of the reaction medium. The extraction step may also be preceded with a salting out effected with a salt such as sodium chloride or sodium sulfate. The salts of the compound of formula I may be prepared by reaction with the corresponding bases in approximately stoichiometric proportions.

A preferred mode of the process of the invention to produce a compound of formula I or a salt comprises reacting the sodium salt of cephalosporin C in the fermentation medium used to produce cephalosporin C and extracting the desired product with n-butanol.

The novel process of the invention to produce 7-amino-cephalosporanic acid comprises subjecting a compound of formula I or a salt to conditions capable of cleaving the compound at the 7-amino group to form 7-amino-cephalosporanic acid. The preferred conditions for cleavage are silylation of the compound of formula I or a salt, followed by iminohalogenation and iminoetherification and hydrolysis of the iminoether.

Another process of the invention for the preparation of 7-amino-cephalosporanic acid comprises reacting cephalosporin C or a salt thereof with phthalic anhydride in an aqueous solution, salifying if necessary the mixture, extracting the reaction medium to recover a compound of formula I or a salt and subjecting the latter to cleavage conditions to obtain 7-amino-cephalosporanic acid.

The preferred cleavage conditions comprise reacting the compound of formula I or a salt with a silylation agent, reacting the resulting product with an agent to form the imide chloride, reacting the latter with a low molecular weight alcohol to obtain the corresponding iminoether which is then hydrolyzed to obtain 7-amino-cephalosporanic acid.

Examples of suitable silylation agents are trialkylhalosilanes such as trimethylchlorosilane, dialkyldihalosilanes such as dimethyldichlorosilane and alkyltrihalosilanes such as methyl trichlorosilane. The agent to form the imide chloride may be phosphorus oxychloride, phosphorus pentachloride, phosphorus trichloride, thionyl chloride or oxalyl chloride.

The low molecular weight alcohol to form the iminoether is preferably an alkanol such as methanol, ethanol or n-butanol and the reaction is preferably effected in the presence of a tertiary amine such as triethylamine or dimethylaniline. The hydrolysis of the iminoether is preferably effected in water in the presence of acid or basic catalysts.

The preferred process of the invention for the preparation of 7-amino-cephalosporanic acid comprises reacting the sodium salt of cephalosporin C in the fermentation medium used to produce cephalosporin C with phthalic anhydride, extracting the reaction medium with a low molecular weight alkanol such as n-butanol to recover the compound of formula I or a salt, reacting the latter with a silylation agent such as a trialkylhalosilane such as trimethylchlorosilane, reacting the resulting product with phosphorus pentachloride to form the iminochloride, reacting the latter with a low molecular weight alkanol such as n-butanol to form the iminoether and hydrolyzing the latter.

In the following examples there are described several preferred embodiments to illustrate the invention. However, it is to be understood that the invention is not intended to be limited to the specific embodiments.

EXAMPLE 1

3-(acetyloxymethyl)-7-{[5-(2-carboxyphenyl)-carbonylamino]-5-carboxy-1-oxo-pentyl-amino}-8-oxo-5-thia-1-aza-bicyclo-[4,2,0]-oct-2-ene-2-carboxylic acid 25 g of sodium bicarbonate and then 25 g of phthalic acid anhydride were added with stirring to a solution of 25 g of cephalosporin C in 250 ml of distilled water and the mixture was stirred at 20°–25° C. for one hour and was then filtered. The filtrate was cooled and then 100 ml of n-butanol were added thereto. The pH of the mixture was adjusted to 2 by addition of phosphoric acid and the mixture was stirred for 30 minutes and was then decanted. The butanol phase charged with crystals was recovered and the aqueous phase was extracted twice with 20 ml of n-butanol to recover butanol phases charged with crystals. The 3 butanol phases were successively filtered and the recovered crystals were washed twice with 10 ml of n-butanol and were dried under reduced pressure to obtain 28.12 g of 3-(acetyloxymethyl)-7-{[5-(2-carboxyphenyl)-carbonylamino]-5-carboxy-1-oxo-pentyl-amino}-8-oxo-5-thia-1-aza-bicyclo-[4,2,0]-oct-2-ene-2-carboxylic acid in the form of white crystals.

Analysis: $C_{24}H_{25}N_3O_{11}S$; molecular weight=562.544. Calculated: %C 51.15; %H 4.47; %N 7.45; %S 5.69. Found: 45.6; 4.7; 6.6; 5.7.

The said product was stirred with 10 parts of iced distilled water and the mixture was filtered. The filter was washed with iced distilled water to eliminate salts to obtain the pure product which had the following analysis: %C 51.2, %H 4.6, %N 7.7, %S 5.5.

EXAMPLE 2

3-(acetyloxymethyl)-7-{[5-(2-carboxyphenyl)carbonylamino]-5-carboxy-1-oxo-pentyl-amino}-8-oxo-5-thia-1-aza-bicyclo-[4,2,0]-oct-2-ene-2-carboxylic acid One liter of a filtered fermentation broth containing 8 g of cephalosporin C was adjusted to a pH of 3, was filtered and the pH was then readjusted to a pH of 8.210 g of phthalic acid anhydride and 10 g of sodium bicarbonate were added to the mixture which was then stirred for one hour. 200 ml of n-butanol were added thereto and the pH was adjusted to 4 by addition of 10% sulfuric acid. The n-butanol phase was decanted and the aqueous phase was extracted twice with 200 ml of n-butanol after the pH was adjusted to 2 with 10% sulfuric acid. The combined ethanolic phases were washed with water and 20 ml of water were added thereto. The mixture was adjusted to a pH of 4 by addition of 2 N sodium hydroxide solution and another 30 ml of water were added thereto. 100 ml of the aqueous phase was adjusted to a pH of 2 by addition of sulfuric acid and 10 ml of n-butanol were added thereto. The mixture was stirred for 3 hours at 0° to 5° C. and was filtered. The recovered product was washed with water and dried to obtain 2.32 g of product identical to that of Example 1.

EXAMPLE 3 sodium 3-(acetyloxymethyl)-7-{[5-(2-carboxyphenyl)-carbonylamino]-5-carboxy-1-oxo-pentyl-amino}-8-oxo-5-thia-1-aza-bicyclo-[4,2,0]-oct-2-ene-2-carboxylate 1 liter of a filtered fermentation medium containing 10 g of cephalosporin C was adjusted to a pH of 7.5 by addition of 2 N sodium hydroxide solution and 20 g of phthalic acid anhydride were added thereto. The mixture was held for one hour with a pH of 7.5 and the pH was then adjusted to 2. Then, 20 g of sodium sulfate were added thereto and the mixture was extracted 4 times with 50 ml of n-butanol. The combined n-butanol extracts were washed 3 times with 50 ml of water and were dehydrated by distillation under reduced pressure. The pH was adjusted to 4 by addition of a solution of sodium ethylhexanoate containing 10% butanol and the mixture was filtered. The recovered product was washed with n-butanol and dried to obtain sodium 3-(acetyloxymethyl)-7-{[5-(2-carboxyphenyl)-carbonylamino]-5-carboxy-1-oxo-pentylamino}-8-oxo-5-thia-1-aza-bicyclo-[4,2,0]-oct-2-ene-2-carboxylate.

EXAMPLE 4

7-amino-cephalosporanic acid 2.8 g of the product of Example 1 were added with stirring under nitrogen to 11 ml of anhydrous methylene chloride and 5.1 ml of dimethylaniline were added thereto. 2.4 ml of trimethylchlorosilane were added to the mixture with stirring under nitrogen and the mixture was stirred at 35° C. for 45 minutes and was then cooled to 20° C. Another 0.7 ml of dimethylaniline and 1 ml of trimethylchlorosilane were added thereto and the mixture was stirred for 1½ hours at room temperature and was then allowed to stand for 18 hours. The mixture was cooled to −65° C. with stirring under nitrogen and then 2.34 g of phosphorus pentachloride were added thereto. The temperature was allowed to rise to −40° C. and after stirring the mixture for 2 hours at −40° C., the mixture was cooled to −65° C. and 20 ml of n-butanol were added thereto. The temperature was again allowed to rise to −40° C. and after stirring for 2 hours at −40° C., 10 ml of demineralized water were added thereto. The temperature was allowed to rise to 20° C. and the mixture was stirred while the pH was adjusted to 3.3 by addition of triethylamine. The mixture stood overnight and was then vacuum filtered. The recovered product was washed with demineralized water, then with acetone and was dried under reduced pressure to obtain 0.9 g of 7-amino-cephalosporanic acid.

Various modifications of the products and processes of the invention may be made without departing from the spirit or scope thereof and it is to be understood that the invention is intended to be limited only as defined in the appended claims.

I claim:

1. A process for the preparation of 7-amino-cephalosporanic acid comprising reacting cephalosporin C or a salt thereof with phthalic anhydride in an aqueous medium, salifying if necessary the mixture, extracting the reaction mixture to recover a compound selected from the group consisting of the compound of the formula

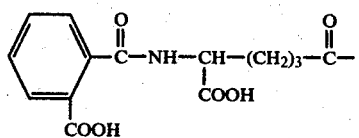

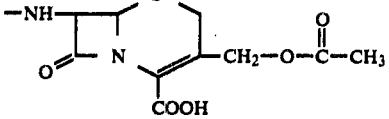

salts thereof selected from the group consisting of alkali metal, alkaline earth metal, ammonium, amine and quaternary ammonium salts and subjecting the latter to cleavage conditions to obtain 7-amino-cephalosporanic acid.

2. The process of claim 1 wherein the extracted compound is reacted with a silylation agent, the resulting product is reacted with an agent to form the corresponding imino chloride, the latter is reacted with a low molecular weight alkanol to form the corresponding iminoether and the latter is hydrolyzed.

3. A process for the preparation of 7-amino-cephalosporanic acid comprising reacting the sodium salt of cephalosporin C in the fermentation medium used to produce cephalosporin C with phthalic anhydride, extracting the reaction medium with a low molecular weight alkanol to recover a compound selected from the group consisting of the compound of the formula

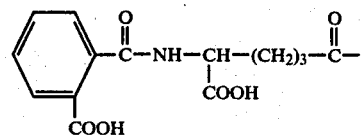

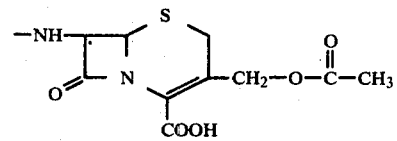

salts thereof selected from the group consisting of alkali metal, alkaline earth metal, ammonium, amine and quaternary ammonium salts, reacting the latter with a silylation agent reacting the resulting product with phosphorus pentachloride to form the imido chloride, reacting the latter with a lower molecular weight alkanol to form the corresponding imino ether and hydrolyzing the latter to form 7-amino-cephalosporanic acid.

* * * * *